US00PP31972P2

(12) United States Plant Patent
Bergman

(10) Patent No.: US PP31,972 P2
(45) Date of Patent: Jul. 14, 2020

(54) ***CHRYSANTHEMUM* PLANT NAMED 'CIDZ0099'**

(50) Latin Name: ***Chrysanthemum* x *morifolium***
Varietal Denomination: CIDZ0099

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/501,432

(22) Filed: Apr. 15, 2019

(51) Int. Cl.
*A01H 5/02* (2018.01)
*A01H 6/14* (2018.01)

(52) U.S. Cl.
USPC ..... Plt./286

(58) Field of Classification Search
USPC ..... Plt./286
CPC ..... A01H 5/0255; A01H 5/02; A01H 5/00; A01H 6/14; A01H 6/1424
See application file for complete search history.

(56) References Cited

U.S. PATENT DOCUMENTS

PP21,481 P2 * 11/2010 Bergman ..... A01H 6/1424 Plt./286

* cited by examiner

*Primary Examiner* — June Hwu
(74) *Attorney, Agent, or Firm* — Dale Skalla

(57) ABSTRACT

A new *Chrysanthemum* plant named 'CIDZ0099' particularly distinguished by its medium size red and yellow bicolored daisy-type inflorescences, strong and uniform plant habit, and a flowering response time of 7.5 weeks.

1 Drawing Sheet

Latin name of the genus and species of the plant claimed: *Chrysanthemum* x *morifolium.*

Varietal denomination: 'CIDZ0099'.

BACKGROUND OF THE NEW PLANT

The present invention comprises a new *Chrysanthemum*, botanically known as *Chrysanthemum* x *morifolium*, and hereinafter referred to by the variety name 'CIDZ0099'.

'CIDZ0099' is a product of a planned breeding program. The new cultivar has medium size red and yellow bicolored daisy-type inflorescences, strong and uniform plant habit, and a flowering response time of 7.5 weeks.

'CIDZ0099' originated as a natural whole plant mutation discovered among flowering plants of 'B9630' growing in a greenhouse in Gilroy, Calif., in November, 2015. The parent is the proprietary plant designated as 'B9630', having purple and white bicolored daisy inflorescences, while it's similar to 'CIDZ0099' in all other characteristics.

The first act of asexual reproduction of 'CIDZ0099' was accomplished when vegetative stem cuttings were propagated from the initial selection in February 2016 in Gilroy Calif.

BRIEF SUMMARY OF INVENTION

Horticultural examination of plants grown from cuttings of the plant initiated in February, 2016 and continuing thereafter, has demonstrated that the combination of characteristics as herein disclosed for 'CIDZ0099' are firmly fixed and are retained through successive generations of asexual reproduction.

'CIDZ0099' has not been observed under all possible environmental conditions. The phenotype may vary significantly with variations in environment such as temperature, light intensity and day length.

A Plant Breeder's Right for this cultivar has not yet been applied for. 'CIDZ0099' has not been made publicly available prior to the effective filing date of this application, notwithstanding any disclosure that may have been made less than one year prior to the effective filing date of this application by the inventor or another who obtained 'CIDZ0099' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0099' with colors being as true as possible with an illustration of this type. The photographic drawing shows in FIG. 1 a close-up view plant of an inflorescence, and in FIG. 2 a flowering plant of the new variety.

DETAILED BOTANICAL DESCRIPTION

The plant descriptions and measurements were taken indoors in Gilroy, Calif. in March, 2019 on about 11 week old plants. Unrooted cuttings had been planted, 4 plants per pot, in 6 inch pots on Dec. 27, 2018. The plants were pinched and moved to short days on Jan. 16, 2019 to induce flowering.

Figure 1:
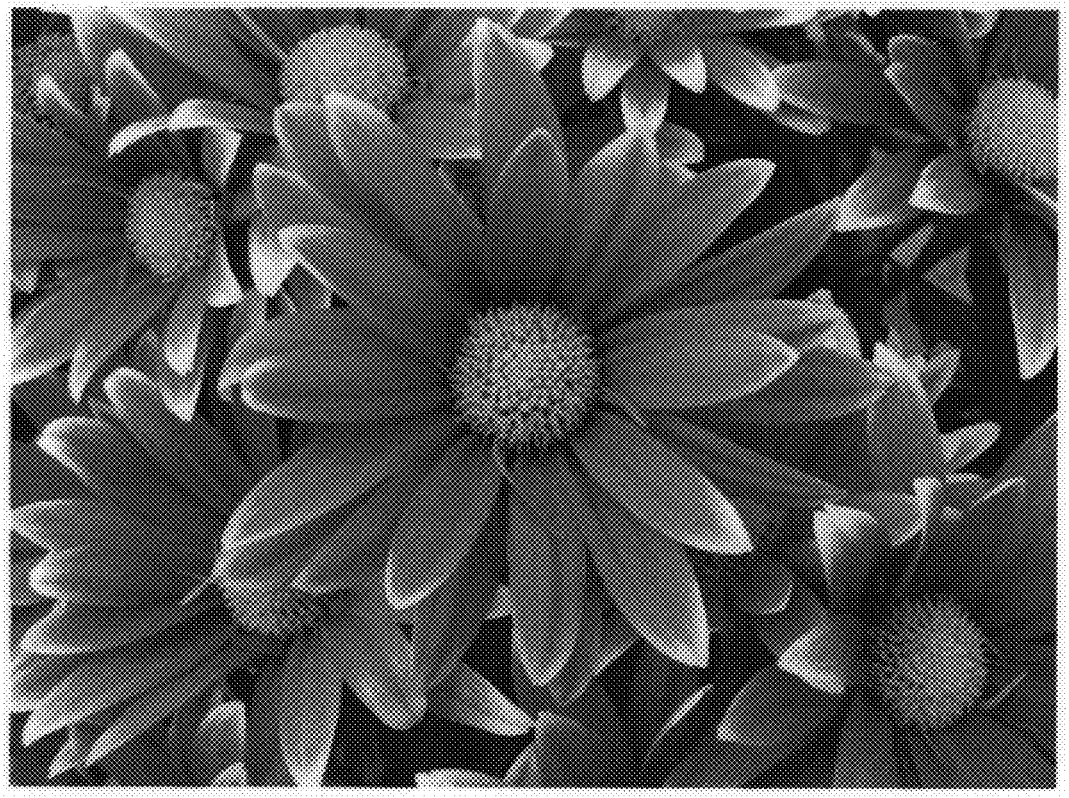
Figure 2:
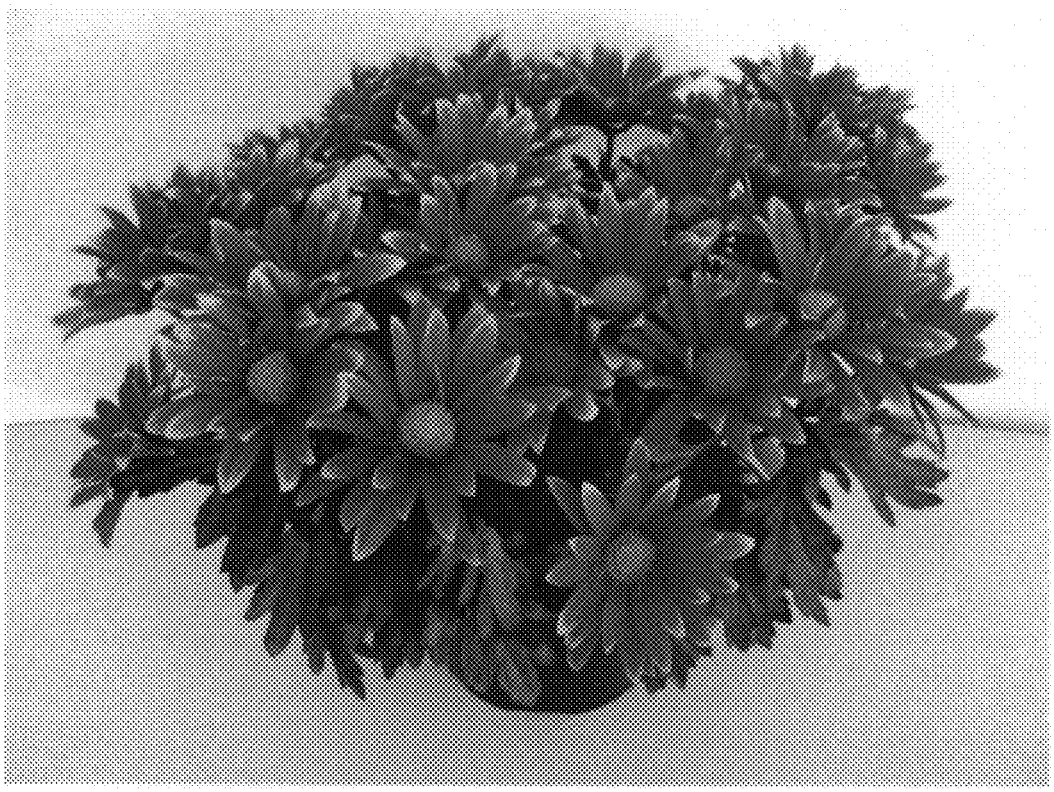

The aforementioned photographs: FIGS. 1 and 2 were taken in Gilroy, Calif. in March 2019, and showing a plant from a trial, in which flowering had been induced by applying black cloth.

These plants were about 11 weeks of age. Unrooted cuttings had been planted, 4 plants per pot, in 6 inch pots. The plants were pinched and moved to short days to induce flowering.

Color references are made to The Royal Horticultural Society Colour Chart (R.H.S.) 2001.

TABLE 1

DIFFERENCES BETWEEN THE NEW VARIETY 'CIDZ0099' AND A MOST SIMILAR VARIETY:

| | 'CIDZ0099' | 'Yosanta Cruz', U.S. Plant Pat. No. 21,481 |
|---|---|---|
| Flower height: | Shorter | Taller |
| Flower response: | 7.5 weeks | 8.5 weeks |
| Plant width: | 28-32 cm | 24-28 cm |
| Inflorescences: | Red and yellow bicolored | Bright orange-red and yellow bicolored |

Plant:

*Form, growth and habit.*—Herbaceous pot-type, stems upright, freely branching, strong and moderately vigorous growth habit.

*Plant height.*—12.0-14.0 cm.

*Plant height (inflorescence included).*—17.0-19.0 cm.

*Plant width.*—28.0-32.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137B.

*Lower surface.*—RHS 137C.

*Mature, leaf color, upper surface.*—RHS 139A.

*Lower surface.*—RHS 138A.

*Length.*—5.5-6.5 cm.

*Width.*—3.8-5.2 cm.

*Shape.*—Ovate.

*Base shape.*—Attenuate.

*Apex shape.*—Mucronate.

*Length of terminal leaf lobe.*—Medium-long.

*Petiole attitude.*—Horizontal.

*Margin.*—Palmately lobed; irregularly incised, somewhat serrate.

*Leaf margin depth.*—Medium.

*Leaf margin indentation.*—Medium.

*Depth of lowest lateral sinus.*—Medium.

*Stipule.*—Very small.

*Texture, upper surface.*—Bifid T-shaped hairs.

*Lower surface.*—Bifid T-shaped hairs.

*Color of veins, upper surface.*—RHS 137C.

*Color of veins, lower surface.*—RHS 138B.

*Pattern of veining.*—Palmate.

*Petiole color.*—RHS 137B.

*Length.*—2.0-2.6 cm.

*Diameter.*—0.2 cm.

*Texture, upper and lower petiole surfaces.*—Bifid T-shaped hairs.

Stem:

*Quantity of main branches per plant.*—4-5.

*Color of stem.*—RHS 138B.

*Length of stem.*—9.0-12.0 cm.

*Diameter.*—0.3-0.6 cm.

*Length of internodes.*—0.5-1.5 cm.

*Texture.*—Bifid T-shaped hairs.

*Color of peduncle.*—RHS 138B.

*Length of peduncle.*—2.8-4.0 cm.

*Peduncle diameter.*—0.15-0.2 cm.

*Texture.*—Bifid T-shaped hairs.

Inflorescence:

*Type.*—Compositae type, solitary daisy-type inflorescences borne terminally above foliage, ray florets arranged acropetally on a capitulum.

*Quantity of short days to flowering (response time).*—7.5 weeks.

*Natural season flowering.*—Not determined on this variety.

*Quantity of inflorescences per plant.*—40-43.

*Lastingness of individual blooms on the plant.*—4 weeks.

*Fragrance.*—Slightly spicy.

Bud (just when opening/showing color):

*Color.*—Closest to RHS 183B.

*Length.*—1.3-1.7 cm.

*Width.*—0.9 cm.

*Shape.*—Oblate.

Immature inflorescence:

*Diameter.*—5.4-6.2 cm.

*Color of ray florets, upper surface.*—Closest to RHS 187D with RHS 5A at the apex.

*Lower surface.*—Closest to RHS 187D overlain with RHS 161D.

Mature inflorescence:

*Diameter.*—7.2-8.5 cm.

*Depth.*—2.5-3.0 cm.

*Total diameter of disc.*—1.7-1.8 cm.

*Average diameter of disc.*—1.75 cm.

*Receptacle color.*—RHS 145B.

*Receptacle height.*—0.6-0.7 cm.

*Receptacle diameter.*—0.9-1.0 cm.

Ray florets:

*Average quantity of florets.*—19-24.

*Color of florets, upper surface.*—RHS 53A and RHS 53C with RHS 5A on the apex.

*Lower surface.*—Closest to RHS 187D overlain with RHS 161D.

*Predominant type of ray floret.*—Ligulate.

*Longitudinal axis of ray floret.*—Straight.

*Length.*—3.4-4.1 cm.

*Width.*—0.8-0.9 cm.

*Length of corolla tube.*—Short.

*Shape.*—Eliptical.

*Apex shape.*—Both acute and emarginate types.

*Margin.*—Entire.

*Texture, upper surface.*—Papillose, 2 shallow keels.

*Lower surface.*—Papillose.

Disc florets:

*Average quantity of florets.*—180-200.

*Color of florets.*—RHS 12A apex; RHS 144B basal.

*Length.*—0.4-0.6 cm.

*Width.*—0.15-0.3 cm when open.

*Shape.*—Tubular, elongated.

*Apex shape.*—Acute, 5 pointed.

Phyllaries:

*Quantity.*—21-26.
*Color, upper surface.*—RHS 137C.
*Lower surface.*—RHS 137B.
*Length.*—0.7-1.0 cm.
*Width.*—0.2-0.3 cm.
*Shape.*—Lanceolate.
*Apex shape.*—Acute.
*Base.*—Fused.
*Margins.*—Entire; slightly papery.
*Texture, upper surface.*—Glabrous.
*Lower surface.*—Bifid T-shaped hairs.

Reproductive organs:

*Pistil.*—1, found on both types of florets.
*Length.*—0.6 cm.
*Style color.*—RHS 155C.
*Style length.*—0.45 cm.
*Stigma color.*—RHS 17C.
*Stigma shape.*—Bi-parted.
*Ovary color.*—RHS 155C but more translucent.
*Stamens.*—4, found on only on the disc florets.
*Color of filaments.*—RHS 155C.
*Length filaments.*—0.4-0.5 cm.
*Anther color.*—RHS 15A.
*Anther length.*—0.15 cm.
*Anther shape.*—Oval.
*Color of pollen.*—RHS 17B.
*Pollen amount.*—Sparse.
*Fertility/seed set.*—Has not been observed to date.
*Disease/pest resistance.*—Has not been observed to date.
*Plant hardiness zone.*—Has not been determined.

What is claimed is:

1. A new and distinct variety of *Chrysanthemum* plant named 'CIDZ0099' substantially as illustrated and described herein.

* * * * *